United States Patent [19]

Morgan

[11] Patent Number: 4,539,092

[45] Date of Patent: Sep. 3, 1985

[54] PLASMA OXYGEN PERMEABILITY METER

[76] Inventor: Louis W. Morgan, P.O. Box 5129, San Francisco, Calif. 94101

[21] Appl. No.: 549,021

[22] Filed: Nov. 7, 1983

[51] Int. Cl.$^3$ ............................................. G01N 27/48
[52] U.S. Cl. ..................................... 204/415; 204/403
[58] Field of Search ............... 204/403, 415, 418, 431, 204/432, 408; 128/635

[56] References Cited

U.S. PATENT DOCUMENTS

| | | | |
|---|---|---|---|
| 3,223,597 | 12/1965 | Hersch | 204/431 X |
| 4,029,563 | 6/1977 | Binder et al. | 204/1 F X |
| 4,042,464 | 8/1977 | Blurton et al. | 204/1 F X |
| 4,126,531 | 11/1978 | Porter et al. | 204/415 X |
| 4,127,462 | 11/1978 | Blurton et al. | 204/412 |
| 4,185,620 | 1/1980 | Hagihara | 204/415 X |
| 4,265,714 | 5/1981 | Nolan et al. | 204/1 B |
| 4,285,796 | 8/1981 | Stoner et al. | 204/412 X |
| 4,400,258 | 8/1983 | Hans-Jurgen et al. | 204/415 X |
| 4,407,291 | 10/1983 | Hagihara et al. | 204/403 X |

Primary Examiner—G. L. Kaplan
Assistant Examiner—Nam X. Nguyen
Attorney, Agent, or Firm—David Pressman; Robert J. Bennett; J. Eppa Hite, III

[57] ABSTRACT

A polarographic oxygen detection cell of the type having concentric coplanar electrodes. The cell achieves more consistent and predictable operation by using electrode insulators to prevent electrochemical reaction between the areas of high charge density on the cathode and anode conduction disk and those portions of the electrolyte in which increased ion concentration has been attracted by this high charge density, and using the OH$^-$ based electrolyte and a carbon anode so that the reaction at the anode produces gas which can be bled off to avoid altering the composition of the anode or electrolyte.

14 Claims, 10 Drawing Figures

PLASMA OXYGEN PERMEABILITY METER

BACKGROUND OF THE INVENTION

1. Field Of The Invention

The present invention relates to devices for measuring oxygen mixed in fluids, and particularly to measuring the rate of oxygen permeation through blood plasma.

2. Prior Art

Conventional devices for detecting oxygen mixed with other gases or dissolved in a liquid have used an electrochemical cell with an oxygen permeable membrane adjacent the cathode. The sample of fluid to be analyzed is placed on the outside of the membrane. Oxygen diffuses through the membrane, into the electrolyte, and is reduced at the cathode, causing an electron flow to the anode. The cell may be either Galvanic, with a voltage increase towards the anode and generating electricity, or polarographic with a voltage decrease towards the anode and requiring an external power supply. Either way, the resultant current is proportional to the amount of oxygen diffusing through the membrane, and is thus a measure of the partial pressure of oxygen in the sample fluid. However, electrochemical probes are slow to reach an equilibrium value in contact with a specimen, particularly a blood specimen. During the interim, the consumption of oxygen in the electrolytic reaction lowers the concentration of oxygen in the sample and distorts the measurement.

Prior art blood-oxygen detectors have tried to avoid altering the sample oxygen partial pressure ($pO_2$) by stirring as in U.S. Pat. No. 4,209,300, or by using a Clark-type polarographic cell with an extremely small cathode surface as in U.S. Pat. Nos. 4,209,300 and 4,207,146. Besides minimizing oxygen consumption, detectors disclosed in U.S. Pat. No. 4,042,465 (Morong), U.S. Pat. No. 4,120,770 (Kessler), U.S. Pat. No. 3,929,588 (Parker), and U.S. Pat. No. 4,264,328 (Marsoner) compensate for consumption in calculating the partial pressure. In the latter three patents, this compensation assumes a fixed diffusion rate of $O_2$ through blood.

Because the prior art devices measure the concentration (solubility) of oxygen by minimizing oxygen consumption and assuming a negligible or fixed diffusion value, they are unsuitable for measuring diffusion, or permeability, which equals the product of diffusivity and solubility. In measuring diffusion or permeability, a tester must act as an oxygen sink and consume as much oxygen as possible, to create a concentration gradient. Oxygen consumption increases with current flow. Current through a Galvanic cell with a given load is limited by the intrinsic voltage potential of the cell. Polarographic cells are preferable for diffusion measurements because, with an appropriate external power supply, larger currents can be produced.

A diffusion cell is described by Thomas Robert Stein in *Augmented Diffusion of Oxygen*, Ph.D. Thesis, University of Minnesota, (1968) and also in *Steady-State Oxygen Transport Through Red Blood Cell Suspensions*, Journal of Applied Physiology, Vol. 31, No. 3, pp. 397-402 (1971). The Stein cell comprises a polarographic cell with a cathode formed from one end of a platinum cylinder 3/16 inch in diameter. The cathode is larger than in previous polarographic cells in order to permit a greater diffusion current and inherently more sensitive measurements. A silver anode disk, 1 1/16 inches in outside diameter with a 5/16 inch central hole, surrounds the cathode cylinder. The cathode and anode are held spaced by epoxy resin. The top surfaces of the cylinder, the epoxy, and the disk are in a common plane. The blood sample to be tested is held in a sample well with a TEFLON membrane over the cathode. Between the membrane and the cathode there is a layer of electrolyte-saturated filter paper. A chamber over the sample well allows the atmosphere over the sample to be controlled.

Using flat, annular, concentric and co-planar electrodes, the half-cell reduction reaction at the cathode in the prior art cell was expected to be:

$$O_2 + 2H_2O + 4e^- \rightarrow 4OH^- \qquad (1)$$

and to take place as described by the "Nernst" equation:

$$E = E^\circ - \frac{RT}{nF} \ln Q \qquad (2)$$

where:
E = observed half-cell e.m.f.
E° = standard cell e.m.f.
R = the gas constant
T = the absolute temperature
F = the faraday constant
n = the number of electrons involved in the reaction, and
Q = the reaction quotient.

However, due to various secondary effects, an unacceptably large and unpredictable current, hereinafter known as the residual current, flows through the electrolyte of the Stein cell even in the total absence of oxygen. Prior art detectors with low voltages and currents were able to compensate for residual currents by simply calibrating the detector current to zero in the absence of oxygen. However, in the larger cathode higher current Stein cell, the residual current is higher.

In addition, Stein appears to overlook the fact that the Nernst equation does not directly consider electrode surface charge distribution, in effect assuming that the distribution is consistently equal to the average. However, in a negatively charged electrode, electrons will repel each other and be concentrated in the points furthest from the centroid of the electrode. If the charge distribution is skewed sufficiently, then the increased concentration of electrons could cause an uncalculated reduction of other species in the electrolyte, such as hydrogen ions, and produce a residual current.

Another drawback of the Stein cell is that it will not hold a calibration when used with the commercially available Clark cell electrolyte, buffered KCl. The oxidation reaction at the anode is essentially:

$$4Ag + 4Cl^- \leftrightarrow 4AgCl + 4e^-. \qquad (3)$$

This causes $OH^-$ to accumulate in the electrolyte, and deposits AgCl on the anode, and reduces the conductivity of the cell. These effects are tolerable in cells used with minimum current to measure oxygen concentration but with high currents the Stein cell will not stay in calibration.

SUMMARY OF THE INVENTION

The present invention obtains more consistent and predictable operation by compensating for the unequal distribution of electrostatic charge on the cathode, preventing the deposit of reaction products on the anode, and maintaining constant ion concentration in the electrolyte.

The present invention conforms to the geometry requirements of the Nernst equation and takes the problem of unequal charge distribution into account by providing a cathode extension and insulating it from the electrolyte.

Calibration is maintained by using an $OH^-$ based electrolyte and a carbon anode. The cathode reaction product, $OH^-$, is consumed at the anode, preserving the electrolyte composition. The anode reaction product is carbon oxide gas which may be bled off without leaving a deposit.

The reliability of the cell is further improved through the provision of an inert gas buffer to drain off reaction products and to insulate the cell from extraneous oxygen.

DETAILED DESCRIPTION OF THE PREFERRED EMBODIMENT

Figure 1:
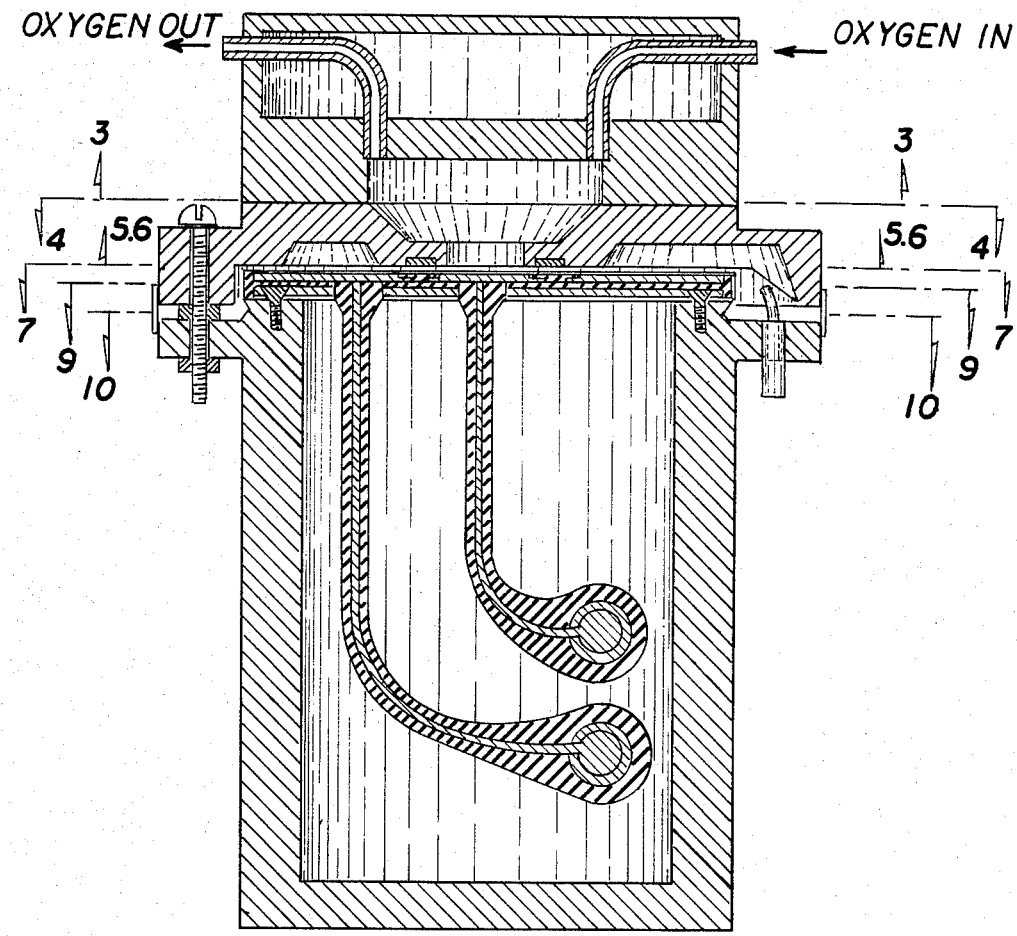
FIG. 1 is a cross-sectional side view of the polarographic oxygen detection cell of the present invention.
Figure 2:
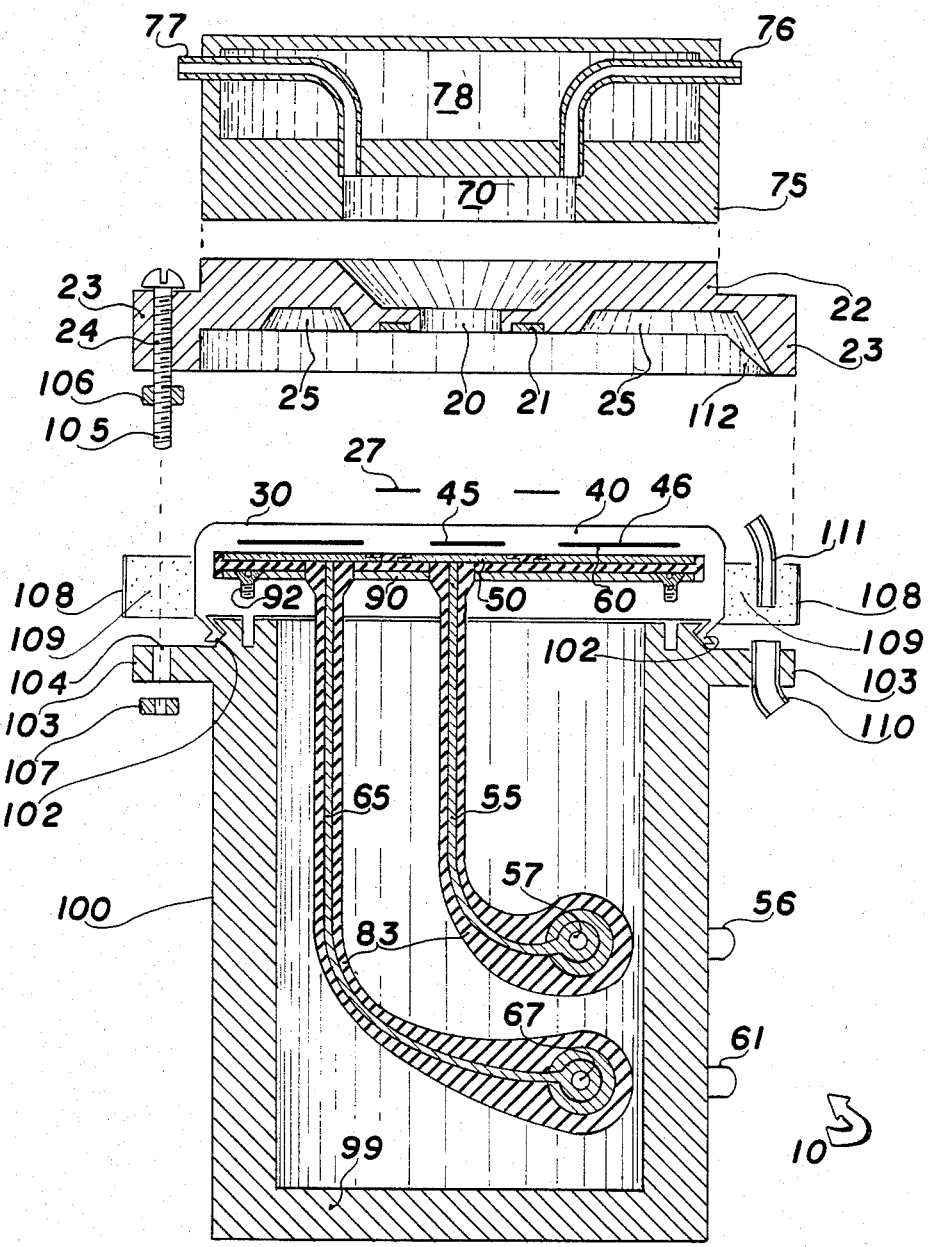
FIG. 2 is an exploded cross-sectional side view of the cell.

The present invention comprises an electrolytic cell, generally denoted 10, useful for measuring the rate at which a liquid is permeated by oxygen. Referring to FIGS. 1 and 2, a known volume, preferably 50 microliters, of liquid such as blood plasma (not shown), is placed in sample well 20 for testing. Oxygen in the sample migrates through a permeable membrane 30 and into an electrolyte solution 40 held by pieces of filter paper 45 and 46 between electrodes 50 and 60 of the cell. An external constant voltage supply (not shown) is used to apply a negative charge to cathode terminal 56 and a positive charge to anode terminal 61. The constant voltage, preferably 0.8000 volt, causes a current through electrolyte 40 in proportion to its oxygen concentration. The current increases to consume greater concentrations. An atmosphere with a known oxygen concentration, preferably pure, is maintained in oxygen chamber 70 over the sample. Oxygen diffusion will tend to compensate for the partial pressure imbalance between the atmosphere in chamber 70 and electrolyte 40, at the rate oxygen reaches the sample layer adjacent membrane 30 and is replenished in electrolyte 40. This determines the current through cell 10 and reflects the oxygen permeability of the sample.

Figure 7:
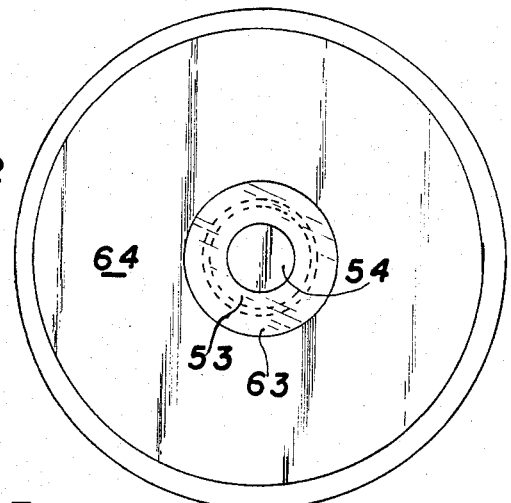
FIG. 7 is a top view of the assembled cell face.
Figure 8:
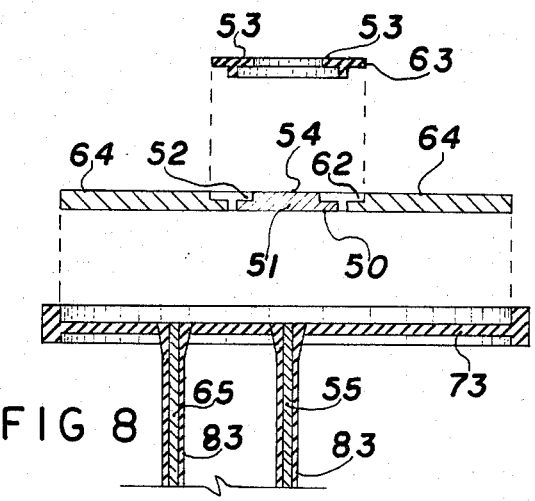
FIG. 8 is an exploded cross-sectional side view of the electrodes and insulators in the cell face.

Residual currents which are believed to occur by an increase in charge density at the circumferential or outer edge of the cathode are suppressed by the present invention through the use of a cathode comprising a sterling silver disk 51, ⅜ inch in diameter and 1/30 inch thick with a 1/16 inch wide rim 52 beveled or otherwise recessed from the face around the perimeter (FIGS. 7 and 8). The exposed central, or "active" area 54 of cathode 50 is ¼ inch in diameter and is polished smooth. Alternatively, a gold cathode may be used. A cathode insulator 53, in the form of (preferably) epoxy, fills recess 52 and forms a cathode high charge density insulator that insulates the electron concentration at the periphery of cathode 50 and suppresses the undue reduction of hydrogen ion by the cathode. The cathode insulator reduces residual current by a factor of about ten.

When a silver anode is used as in the prior art with a potassium chloride electrolyte, chlorine from the electrolyte forms silver chloride on the anode, increasing its resistance. While this is not a problem in low current cells designed to minimize oxygen consumption, the deposit accumulates more quickly under high current operation, as in a diffusivity detector, and interferes with the calibration. Called anode passivation, this problem is minimized in the present invention by forming the anode from carbon layer 60 on filter paper substrate 46. Filter paper substrate 46 is preferably a 1.5 inch diameter circle with a 7/16 inch diameter center hole. Filter paper such as "Whatman 540" is suitable, although it is believed that any fibrous material would also be suitable. The silver anode used in the prior art Stein cell is retained in the present invention as "anode conduction disk" 64 to support carbon layer 60 and to conduct electrons from the carbon layer to anode terminal 61. As much carbon (#3370, available from the J. T. Baker Co.) as possible should be rubbed into the underside of filter paper 46, or anode conduction disk 64 will oxidize. Loose excess carbon should be removed, or it will wash onto active cathode 54 where it will form foci for charge concentration, permit the evolution of hydrogen, and raise the residual current. Although carbon anodes have been reported to form an insulating layer of solid, non-conducting "graphitic oxide," this has not happened in the present invention. Anode conduction disk 64 is preferably sterling silver 1.5 inches in diameter and 1/30 inch thick with a 7/16 inch center hole. If the anode conduction disk were isolated, any charge on it would be concentrated on its outer rim. The negatively-charged cathode at its center, however, concentrates positive charge on the inner edge of conduction disk 64. This ring of high charge is preferably insulated by removing a thin layer of silver from the inner 1/16 inch 62 of the top surface and replacing it with an "anode conduction disk high charge density insulator" 63 of epoxy. Although anode insulator 63 is not as important as cathode insulator 53, it does prevent oxidation of the innermost portion of anode conduction disk 64. Epoxy insulation 73 continues around the sides and bottom of the cathode and anode.

To avoid changes in the composition of electrolyte 40, $OH^-$ ions are used rather than the $Cl^-$ ions used in the prior art. A suitable electrolyte comprises: 1 part 0.28M (isotonic) $NH_4OH$ (ammonium hydroxide) saturated with $Ag_2O$; buffered with 21 parts of 0.162M (isotonic) $NaHCO_3$ (sodium bicarbonate); and a wetting agent such as 1/30th part ("Joy" brand) dish washing detergent. $OH^-$ ions are produced at cathode 50 and consumed at anode 60 with no net effect on electrolyte 40. The half cell reactions are:

$$O_2 + 2H_2O + 4e^- \rightarrow 4OH^- \tag{1}$$

$$4OH^- + C \rightarrow CO_2 + 2H_2O + 4e^-. \tag{4}$$

The reaction product at anode 60 is $CO_2$, or perhaps CO, which may both be bled off, as will be explained, leaving no deposit on the anode.

Figure 9:
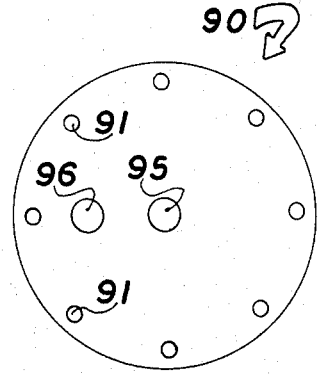
FIG. 9 is a top view of the cell face support plate.
Figure 10:
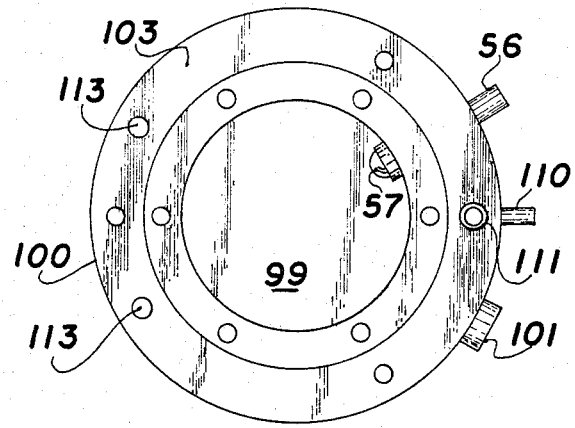
FIG. 10 is a top view of the cell water jacket.

Anode conduction disk 64, cathode 50, and insulating epoxy 53, 63, 73 are mounted on a "cell face support plate" 90, FIG. 9. Support plate 90 is preferably a copper disk 1.5 inches in diameter and 1/40 inch thick. Preferably, the support plate has six countersunk holes 91. Support plate bolts 92 through the holes, their tops ground flush with the top of the support plate 90, and Weldon 40 ® methyl acrylic ester glue preferably hold support plate 90 to the top of the water jacket 100. Water jacket 100, FIG. 10, is preferably an acrylic tube two inches long with an outside diameter of 1.5 inches and an inside diameter of 1 inch. Bottom 99 of the water jacket is an acrylic disk 1.5 inches in diameter and ¼ inch thick.

Cathode connecting wire 55 passes through ⅛ inch center hole 95 in support plate 90, and anode connecting wire 65 passes through ⅛ inch off-center hole 96. Electrode connecting wires 55 and 65 are attached to respective terminals 56 and 61, preferably brass bolts ⅛ inch thick and ¾ inch long. All parts of cathode connecting wire 55, anode connecting wire 65 and electrode connection bolts 57 and 67 inside water jacket 100 are waterproofed with epoxy 83 and silicone rubber (not shown). A pair of hose connector ports 101, preferably brass tubes ¾ inch long and ⅜ inch outside diameter, permit water from an external 37° C. source (not shown) to circulate through ports 101 into water jacket 100 and maintain electrolyte 40 and the sample at a constant temperature. The bottom of cell face support plate 90 is exposed so that it can convey heat as efficiently as possible from the water to the outer ¼ inch of the underside of anode conduction disk 64. Water jacket 100 is surrounded on the outside near the top by rubber band groove 102 which receives a rubber band (not shown) to hold membrane 30 in place, as will be explained. Below groove 102, water jacket 100 is surrounded by an inert gas collar ring 103 made of acrylic 1/16 inch thick with an inside diameter of 1.5 inches and an outside diameter of 2 inches, which is glued to the water jacket.

Cathode 50, anode conduction disk 64 and cell face support plate 90 are permanently glued to water jacket 100. The remainder of cell 10 is reassembled for cleaning or for each use.

The filter paper 46 with carbon layer anode 60 is positioned over anode conduction disk 64, and a 13/32 inch diameter non-carbon coated filter paper center plug 45 is positioned to maintain electrolyte 40 in contact with cathode 50. The distance between the outer edge of plug 45 and the inner edge of the anode filter paper 46 should be small enough that electrolyte 40 can easily bridge the gap. About 20 drops of electrolyte are placed on the anode filter paper 46, and trapped air is rolled out using a glass rod. Cathode 50 is cleaned with a cotton swab to remove any carbon that may have washed onto it, and center plug 45 is positioned and wetted with electrolyte 40.

A conventional semipermeable membrane 30 is used to prevent the sample from altering the electrolyte 40. Polyethylene sheets 1/2000 inch thick, like those used for dry cleaning bags, are suitable. Membrane 30 is slowly unrolled across the wet filter paper without trapping any air bubbles, and pulled down across rubber band groove 102. A rubber band (Eberhard Faber, size number 8) is placed over the membrane to hold it in the groove. The excess membrane below the rubber band should be trimmed off.

Figure 4:
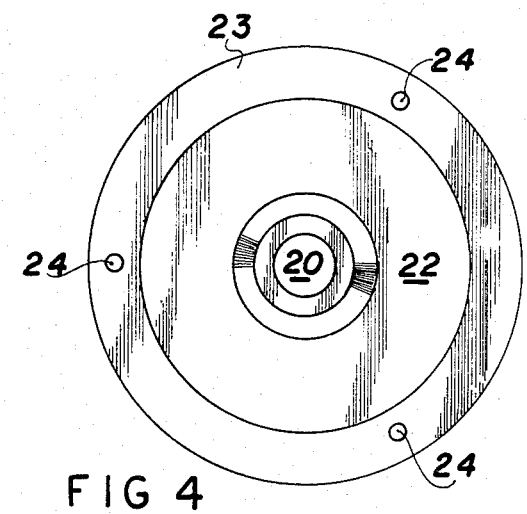
FIG. 4 is a top view of the sample plate and ring.
Figure 5:
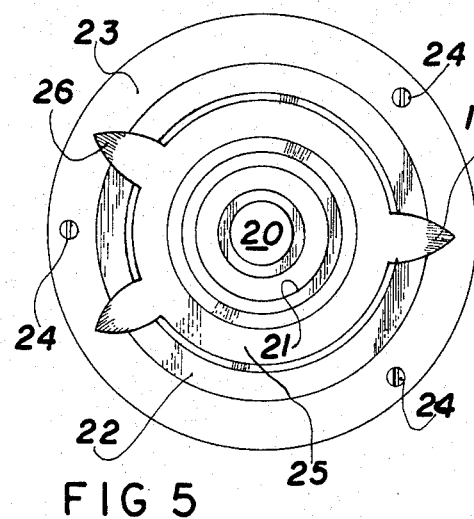
FIG. 5 is a bottom view of the sample plate and ring.
Figure 6:
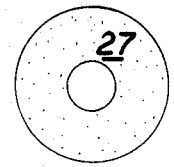
FIG. 6 is a bottom view of the sample well sealing tape.

Sample plate 22, FIGS. 2, 4 and 5, fits over membrane 30. Double-sided tape 27, such as Arno "Tiger Tape" ®, FIG. 6, is placed on the underside of sample plate 22 as shown in FIG. 2. Plate 22 is preferably machined from a copper disk 1.5 inches in diameter and 3/16 inch thick. Alternatively, the plate may be made from acrylic. Together sample plate 22, double-sided tape 27 and membrane 30 form sample well 20 over cathode 50. Sample well 20 preferably has the same volume, 50 microliters, as the samples to be tested, and is ¼ inch in diameter and approximately 0.062 inches deep. The ¼ inch diameter hole in the sample plate 22 forms the upper approximately 0.05 inch of the sample well 20, and the ¼ inch diameter hole in the double-sided tape 27 forms the lower approximately 0.012 inch of the sample well. The two holes are concentric. Tape 27 will prevent the sample from leaking out of sample well 20. Without tape 27, capillary action would draw the sample between the bottom of the sample plate and membrane 30. The portion of the bottom of the sample plate 22 not covered by double-sided tape 27 extends approximately 0.007 inch below the portion to which the tape is applied in order to partially compensate for the thickness of the tape. The sample plate is surrounded by a ¼ inch thick acrylic sample plate ring 23 which has three bolt holes 24. Inert gas collar ring 103 has corresponding holes 104. Bolts 105 are inserted through the ring and collar and anchored by nuts 106, 107 to hold the sample plate, double-sided tape, and membrane against the cell face. The two nuts are tightened to regulate the pressure of the sample plate against the cell face. If the pressure is too great, the sample plate will gradually squeeze the electrolyte from the filter paper and change the response characteristics of the cell. A strip of "inert gas collar tape" 108 is wrapped around the gap between inert gas collar ring 103 and sample plate ring 23 to complete "inert gas collar 109." The prior art cell was not protected from the intrusion of extraneous oxygen.

Although as explained, very little silver oxide is produced at the anode conduction disk, it must be prevented from migrating to the cathode where silver would plate out and cause a misleading increase in the current. A solid copper sample plate prevents this migration, but if an acrylic sample plate is used it is necessary to have a "static charge transfer ring" 21 embedded in the underside of the sample plate as part of the well. Ring 21 is an aluminum torus 0.011 inch thick with an inside diameter of a ¼ inch and an outside diameter of ½ inch.

A ring-shaped cavity in the under side of sample plate 22, generally over anode 60, forms a "reaction product drain" 25, 1/16 inch deep, ⅝ inch inside diameter, and 1.25 inches outside diameter. Carbon oxides formed at anode 60 diffuse back across membrane 30 into cavity 25, avoiding the build-up of reaction products in the cell. Inert gas from an external source, preferably nitrogen, is supplied through inert gas supply tube 110 and extension 111 to inert gas collar 109 and drain entrance 112 to the reaction product drain 25. The reaction product drain and the inert gas collar are purged by a stream of inert gas from the inert gas supply tube extension 111. Collar 109 prevents extraneous oxygen in the environment from entering the cell and causing misleadingly high currents.

The inert gas and entrained reaction products leave drain 25 through reaction product drain exits 26 (FIG. 5), and enter inert gas collar 109. Inert gas coming directly from tube extension 111, and the gas passing through drain 25, both exit inert gas collar 109 through exit holes 113 (FIG. 10) in ring 103, and are vented to the atmosphere.

Figure 3:
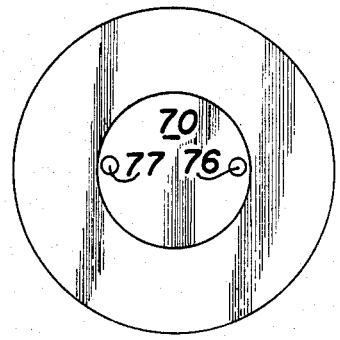
FIG. 3 is a bottom view of the oxygen chamber lid.

Blood plasma samples adhere to the sides of the well, and surface tension draws the top of the sample flat. Once the sample is in place, oxygen chamber lid 75 (FIGS. 1, 2, and 3) is secured over sample plate 22 using a clamp or spring, not shown. The oxygen chamber lid is preferably made from a copper disk 1.5 inch in diameter and ⅜ inch thick. It serves to supply a flow of oxygen at a known concentration from an external source (not shown) through entrance tube 76 to oxygen chamber 70 and out exit tube 77. The chamber is a circular cavity ½ inch in diameter and ⅛ inch deep which provides a space for the controlled atmosphere. Chamber lid 75 also comprises a constant temperature water bath 78 to maintain the oxygen tubes 76 and 77 and the top of sample plate 22 at controlled temperatures.

OPERATION

Once the membrane and sample plate are in place, the cell must calibrated. The cell should be operated at 0.8000 volt with nitrogen passing through oxygen chamber 70 so that oxygen adsorbed onto carbon anode 60 will diffuse to the active cathode 54 and be reduced, allowing an electrical current to pass through the cell. This current will decrease as the adsorbed oxygen is used up until it reaches a minimum in about five hours. The minimum current that the cell passes in the absence of oxygen is called the residual current, $I_r$.

Air saturated with water vapor is then passed through the oxygen chamber 70 for several hours to obtain a reading for the equilibration current $I_e$ due to the residual current $I_r$ plus the air current $I_a$ due to the 20.946% oxygen in air. $I_e = I_a + I_r$.

The calibration current $I_c$ is calculated from the air current $I_a$. The calibration current $I_c$ is the current the cell would pass with water vapor saturated oxygen in oxygen chamber 70 and no sample in the sample well 20. It is not measured directly because high currents cause oxidation of anode conduction disk 64 and speed the accumulation of silver oxide in electrolyte 40. Since air is 20.946% oxygen, $I_c = I_a/0.20946 = 4.7742\ I_a$.

A sample is then placed in sample well, water vapor saturated oxygen is flowed through oxygen chamber 70, and a reading for the measured current $I_m$ is taken. The measured current $I_m$ minus the residual current $I_r$ is equal to the sample current $I_s$ which can be related to oxygen permeability of the liquid sample by the equation:

$$rho = K_w K_o \frac{P_{std}}{P_{atm} - VP_{H2O}} \frac{I_c I_s}{I_c - I_s}$$

where:
rho = the oxygen permeability of the liquid sample.
$K_w$ = the well constant = the height of sample well 20 divided by its cross-sectional area = $h/A = 0.487$ cm$^{-1}$.
$K_o$ = the oxygen constant = the molar volume (22.414 l./gr.-mole) divided by the product of Faraday's constant (96,500 coulombs/equiv.) and the number of electrons exchanged in the reduction of one molecule of oxygen (4 equiv./gram-mole) = $58.1 \times 10^{-3}$ cm$^3$/coulomb.
$P_{std} = 760$ mm Hg.
$P_{atm}$ = the atmospheric pressure at the time the other readings are taken.
$VP_{H2O}$ = the vapor pressure of water at 37° C. = 47.1 mm Hg.
$I_c = 4.7742\ (I_e - I_r)$.
$I_s = I_m - I_r$.
For example, if:
$P_{atm} = 768$ mm Hg.
$I_r = 0.03$ uA (microamps).
$I_e = 8.13$ uA.
$I_m = 13.53$ uA.
Then:

$$K_w K_o = 2.83 \times 10^{-2}\ cm^2/coulomb$$

$$\frac{P_{std}}{P_{atm} - VP_{H2O}} = 1.02$$

$$\frac{I_c I_s}{I_c - I_s} = 2.074 \times 10^{-5}\ coulombs/sec$$

And:

$$rho = 2.83 \times 10^{-2}\ cm^2/coulomb \times 1.02 \times 2.074 \times 10^{-5}\ coulombs/sec$$
$$= 5.99 \times 10^{-7}\ cm^2/sec = \text{oxygen permeability of the sample.}$$

Details have been disclosed to illustrate the invention in a preferred embodiment of which adaptations and modifications within the spirit and scope of the invention will occur to those skilled in the art. The scope of the invention is limited only by the following.

What is claimed:

1. A polarographic cell having substantially uniform electrochemical reactivity on a relatively large planar area, comprising:
   a. an electrical conductor with a planar surface, and
   b. means to compensate for the effect on an electrolyte of unequal distribution of electrostatic charge on said surface by preventing electron transfer across the boundary between said surface and said electrolyte wherever said electrostatic charge on said surface has high enough density to substantially alter the ion concentrations at said boundary, such as to ensure that electrons move across said boundary only where said electrostatic charge has low enough density to permit said ion concentrations at said boundary to be substantially uniform, whereby electrochemical reactions take place in said cell with substantial uniformity as described by the Nernst equation for said substantially uniform ion concentrations.

2. The polarographic cell of claim 1, said means to compensate comprising a layer of electrically insulating material interposed at said boundary wherever said high density of said electrostatic charge substantially alters said ion concentrations at said boundary.

3. The polarographic cell of claim 1 wherein:
   a. said electrical conductor comprises a flat circular disk of electrically conducting material insulated on its edge and back surface, and
   b. said means to compensate comprises a layer of electrically insulating material on the periphery of the front surface of said flat circular disk in addition to the insulation on its edge and back surface, thereby to present a flat circular conductive surface to electrolyte which contains substantially uniform ion concentrations at said conductive surface, whereby said electrochemical reactions in said cell proceed with substantial uniformity as described by the Nernst equation for said substantially uniform ion concentrations on said conductive surface and not as described by said equation for the ion concentrations altered by the high charge density at said periphery of said disk.

4. In a polarographic cell for measuring oxygen permeation through fluid samples held in a sample well, said cell being of the type having generally coplanar sensing and counter electrodes in contact with a common electrolyte, said sensing electrode being a flat circular cathode with a relatively large area surface for quantitatively reducing oxygen, said counter electrode being an annular disk anode substantially concentric to said cathode, the improvements comprising:
  a. means for suppressing an electrical current which would pass through said electrolyte from said cathode to said anode in the absence of oxygen entering said cell through said sample well, and
  b. means for minimizing the accumulation of reaction products within said cell.

5. The polarographic cell of claim 4 wherein said means for suppressing includes:
  a. said cathode having substantially uniform electrochemical reactivity on a relatively large planar area,
  b. means for providing a polarization voltage whose value is such that, on said relatively large planar area, said cathode efficiently reduces oxygen but reduces said electrolyte only very slightly, and
  c. means for preventing oxygen from entering said cell except through said sample well,
  whereby said electrical current passed by said cathode results from said reduction of said oxygen which enters said cell through said sample well, not from said reduction of said electrolyte or from reduction of oxygen which enters said cell other than through said sample well.

6. The polarographic cell of claim 5, wherein said cathode comprising:
  a. an electrical conductor with a planar surface, and
  b. means to compensate for the effect on an electrolyte of unequal distribution of electrostatic charge on said surface by preventing electron transfer across the boundary between said surface and said electrolyte wherever said electrostatic charge on said surface has high enough density to substantially alter the ion concentrations at said boundary, such as to ensure that electrons move across said boundary only where said electrostatic charge has low enough density to permit said ion concentrations at said boundary to be substantially uniform,
  whereby electrochemical reactions take place on said cathode with substantial uniformity as described by the Nernst equation for said substantially uniform ion concentrations.

7. The polarographic cell of claim 5, wherein said cathode comprising:
  a. a flat circular disk of electrically conducting material insulated on its edge and back surface, and
  b. a layer of electrically insulating material on the periphery of the front surface of said flat circular disk in addition to the insulation on its edge and back surface,
  thereby presenting a flat circular conductive surface to the electrolyte which contains substantially uniform ion concentrations at said conductive surface,
  whereby said electrochemical reactions on said cathode proceed with substantial uniformity as described by the Nernst equation for said substantially uniform ion concentrations on said conductive surface and not as described by said equation for the ion concentrations altered by the high charge density at said periphery of said disk.

8. The polarographic cell of claim 5 wherein said means for preventing comprises an inert gas collar through which an inert gas is continually passed around the outer edge of said cell,
  thereby to prevent oxygen from entering said polarographic cell except through said sample well.

9. The polarographic cell of claim 4 wherein said means for minimizing comprises:
  a. said anode including a renewable active surface composed of a carbon layer on a fibrous substrate,
  b. said electrolyte including oxygen-containing negative ions which oxidize said carbon of said active surface as they themselves are being oxidized by said anode, and
  c. means for removing gaseous carbon oxides from said cell,
  whereby the reaction of said electrolyte as an oxidizing agent on said active surface produces said gaseous carbon oxides which diffuse away from said active surface, which do not rereact at said cathode, and which can be bled off from said electrolyte,
  thereby leaving said active surface free from reaction products, preventing rereaction of anodic reaction products at said cathode, and minimizing the change in electrolyte composition resulting from dissolution of said reaction products.

10. The polarographic cell of claim 9 wherein said anode comprises:
  a. an anode conduction disk with substantially uniform electrochemical reactivity, and
  b. said carbon active surface being held in contact with the conductive surface of said anode conduction disk by a removable fibrous matrix,
  thereby: (1) providing for the conduction of electrons away from said carbon layer without reducing its surface area; (2) preventing the migration of said carbon to other parts of said cell; and (3) facilitating renewal of said active surface.

11. The polarographic cell of claim 10, wherein said anode conduction disk comprising:
  a. an electrical conductor with a planar surface, and
  b. means to compensate for the effect on an electrolyte of unequal distribution of electrostatic charge on said surface by preventing electron transfer across the boundary between said surface and said electrolyte wherever said electrostatic charge on said surface has high enough density to substantially alter the ion concentrations at said boundary, such as to ensure that electrons move across said boundary only where said electrostatic charge has low enough density to permit said ion concentrations at said boundary to be substantially uniform,
  whereby electrochemical reactions take place on said anode conduction disk with substantial uniformity as described by the Nernst equation for said substantially uniform ion concentrations.

12. The polarographic cell of claim 10 wherein said anode conduction disk comprises:
   a. a flat circular disk insulated on its edges and back surface having a concentric circular hole, and
   b. a layer of electrically insulating material surrounding said concentric circular hole on the front surface of said flat circular disk in addition to said insulation on its edges and back surface,
   thereby preventing electron exchange between said anode conduction disk and those portions of said electrolyte in which the ion concentrations have been altered by the high charge density on the inner edge of said anode conduction disk,
   whereby said anode conduction disk does not react quantitatively with said electrolyte but only serves to convey electrons away from said active surface of carbon,
   thereby preventing the ionization of the atoms of said anode conduction disk to form positive ions which would diffuse to said cathode where their electrochemical reduction would increase said current which passes through said electrolyte from said cathode to said anode in the absence of oxygen entering said cell through said sample well.

13. The polarographic cell of claim 9 wherein said oxygen-containing negative ions comprising:
   a. hydroxide ions ($OH^-$) as electrochemically active negative ions, and
   b. bicarbonate ions ($HCO_3^-$) as negative ions which buffer said electrolyte.
   whereby the reaction of said hydroxide ions with said active surface not only produces said gaseous carbon oxides but also consumes the hydroxide ions produced at said cathode,
   thereby preventing the accumulation of cathodic reaction products in said cell, and
   whereby those gaseous carbon oxides which dissolve in said electrolyte are in chemical equilibrium with said bicarbonate buffer ions,
   thereby minimizing the change in the composition of said electrolyte caused by a fraction of said gaseous carbon oxides which is retained in said electrolyte.

14. The polarographic cell of claim 9 wherein said means for removing comprising a reaction product drain through which an inert gas continually passes in close proximity to said anode,
   thereby maximizing the removal of gaseous anode reaction products from said electrolyte.

* * * * *